(12) United States Patent
Altshuler et al.

(10) Patent No.: US 6,723,090 B2
(45) Date of Patent: Apr. 20, 2004

(54) FIBER LASER DEVICE FOR MEDICAL/ COSMETIC PROCEDURES

(75) Inventors: Gregory B. Altshuler, Wilmington, MA (US); Andrei V. Erofeev, North Andover, MA (US); Ilya Yaroslavsky, Marlborough, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 0 days.

(21) Appl. No.: 10/188,319

(22) Filed: Jul. 2, 2002

(65) Prior Publication Data

US 2003/0055413 A1 Mar. 20, 2003

Related U.S. Application Data

(60) Provisional application No. 60/302,426, filed on Jul. 2, 2001.

(51) Int. Cl.[7] .............................................. A01B 18/22
(52) U.S. Cl. .............................. 606/9; 606/11; 128/898
(58) Field of Search ...................... 372/6, 20; 606/9–11

(56) References Cited

U.S. PATENT DOCUMENTS

| | | |
|---|---|---|
| 3,327,712 A | 6/1967 | Kaufman et al. |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,818,914 A | 6/1974 | Bender |
| 3,834,391 A | 9/1974 | Block |
| 3,900,034 A | 8/1975 | Katz et al. |
| 4,233,493 A | 11/1980 | Nath |
| 4,273,109 A | 6/1981 | Enderby |
| 4,316,467 A | 2/1982 | Muckerheide |
| 4,388,924 A | 6/1983 | Weissman et al. |
| 4,461,294 A | 7/1984 | Baron |

(List continued on next page.)

FOREIGN PATENT DOCUMENTS

| | | |
|---|---|---|
| EP | 0142671 A1 | 5/1985 |
| EP | 0565331 A2 | 10/1993 |
| EP | 0598984 A1 | 6/1994 |
| EP | 0724894 A2 | 8/1996 |
| EP | 0726083 A2 | 8/1996 |
| EP | 0736308 A2 | 10/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |
| EP | 1219258 A1 | 7/2002 |
| GB | 2044908 A | 10/1980 |
| GB | 2123287 A | 2/1984 |
| GB | 2360946 A | 10/2001 |

(List continued on next page.)

OTHER PUBLICATIONS

G.B. Altshuler et al., "Acoustic response of hard dental tissues to pulsed laser action," SPIE, vol. 2080, Dental Application of Lasers, pp. 97–103, 1993.

G.B. Altshuler et al., "Extended theory of selective photothermolysis," Lasers in Surgery and Medicine, vol. 29, pp. 416–432, 2001.

R.L. Army & R. Storb, "Selective mitochondrial damage by a ruby laser microbeam: An electron microscopic study," Science, vol. 15, pp. 756–758, Nov. 1965.

(List continued on next page.)

*Primary Examiner*—Michael Peffley
*Assistant Examiner*—Henry M. Johnson, III
(74) *Attorney, Agent, or Firm*—Thomas J. Engellenner; Deborah A. Miller; Nutter, McClennen & Fish, LLP

(57) ABSTRACT

A method and apparatus are provided for radiation treatment on a patient by use fiber laser and/or a tunable laser, a tunable fiber laser being used for preferred embodiments. Wavelength may be controlled to control depth of penetration and/or radiation absorption and may be scanned to scan depth of penetration.

26 Claims, 5 Drawing Sheets

U.S. PATENT DOCUMENTS

| | | |
|---|---|---|
| 4,539,987 A | 9/1985 | Nath et al. |
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,747,660 A | 5/1988 | Nishioka et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,917,084 A | 4/1990 | Sinofsky |
| 4,926,227 A | 5/1990 | Jensen |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,218,610 A * | 6/1993 | Dixon .......................... 372/20 |
| 5,225,926 A | 7/1993 | Cuomo et al. |
| 5,226,907 A | 7/1993 | Tankovich |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,531,739 A | 7/1996 | Trelles |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,658,323 A | 8/1997 | Miller |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse et al. |
| 5,849,029 A | 12/1998 | Eckhouse et al. |
| 5,853,407 A | 12/1998 | Miller |
| 5,885,211 A | 3/1999 | Eppstein et al. |
| 5,885,273 A | 3/1999 | Eckhouse et al. |
| 5,885,274 A | 3/1999 | Fullmer et al. |
| 5,944,748 A | 8/1999 | Mager et al. |
| 5,948,011 A | 9/1999 | Knowlton |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 6,015,404 A | 1/2000 | Altshuler et al. |
| 6,027,495 A | 2/2000 | Miller |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,096,029 A | 8/2000 | O'Donnell, Jr. |
| 6,096,209 A | 8/2000 | O'Brien et al. |
| 6,104,959 A | 8/2000 | Spertell |
| 6,120,497 A | 9/2000 | Anderson et al. |
| 6,149,644 A | 11/2000 | Xie |
| 6,174,325 B1 | 1/2001 | Eckhouse |
| 6,197,020 B1 | 3/2001 | O'Donnell |
| 6,200,309 B1 | 3/2001 | Rice et al. |
| 6,229,831 B1 | 5/2001 | Nightingale et al. |
| 6,235,016 B1 | 5/2001 | Stewart |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,304,585 B1 | 10/2001 | Sanders et al. |
| 6,306,130 B1 | 10/2001 | Anderson et al. |
| 6,354,370 B1 | 3/2002 | Miller et al. |
| 6,406,474 B1 * | 6/2002 | Neuberger et al. ............. 606/9 |
| 6,508,813 B1 | 1/2003 | Altshuler |
| 6,511,475 B1 | 1/2003 | Altshuler et al. |
| 6,517,532 B1 | 2/2003 | Altshuler et al. |
| 6,547,780 B1 * | 4/2003 | Sinofsky ...................... 606/10 |
| 6,556,596 B1 * | 4/2003 | Kim et al. ..................... 372/6 |

FOREIGN PATENT DOCUMENTS

| | | |
|---|---|---|
| RU | 2089126 C1 | 10/1997 |
| RU | 2089127 | 10/1997 |
| WO | WO 86/02783 | 5/1986 |
| WO | WO 90/00420 | 1/1990 |
| WO | WO 92/16338 | 1/1992 |
| WO | WO 92/19165 | 11/1992 |
| WO | WO 93/05920 | 4/1993 |
| WO | WO 95/15725 | 6/1995 |
| WO | WO 95/32441 | 11/1995 |
| WO | WO 96/23447 | 8/1996 |
| WO | WO 97/13458 | 4/1997 |
| WO | WO 98/04317 | 2/1998 |
| WO | WO 98/24507 | 6/1998 |
| WO | WO 98/51235 | 11/1998 |
| WO | WO 98/52481 | 11/1998 |

| WO | WO 99/27997 A1 | 6/1999 |
| --- | --- | --- |
| WO | WO 99/29243 | 6/1999 |
| WO | WO 99/38569 | 8/1999 |
| WO | WO 99/46005 | 9/1999 |
| WO | WO 99/49937 A1 | 10/1999 |
| WO | WO 00/03257 | 1/2000 |
| WO | WO 00/71045 A1 | 11/2000 |
| WO | WO 00/74781 A1 | 12/2000 |
| WO | WO 00/78242 A1 | 12/2000 |
| WO | WO 01/03257 A1 | 1/2001 |
| WO | WO 01/34048 A1 | 5/2001 |
| WO | WO 01/54606 A1 | 8/2001 |
| WO | WO 02/53050 A1 | 7/2002 |
| WO | WO 02/094116 A1 | 11/2002 |

OTHER PUBLICATIONS

R.R. Anderson et al., "The optics of human skin," Journal of Investigative Dermatology, vol. 77, No. 1, pp. 13–19, 1981.

R.R. Anderson & J.A. Parrish, "Selective photothermolysis: Precise microsurgery by selective absorption of pulsed radiation," Science, vol. 220, pp. 524–527, Apr. 1983.

A.V. Belikov et al., "Identification of enamel and dentine under tooth laser treatment," SPIE vol. 2623, Progress in Biomedical Optics Europe Series, Proceedings of Medical Applications of Lasers III, pp. 109–116, Sep. 1995.

J.S. Dover et al., "Pigmented guinea pig skin irradiated with Q–switched ruby laser pulses," Arch Dermatol, vol. 125, pp. 43–49, Jan. 1989.

L.H. Finkelstein & L.M. Blatstein, "Epilation of hair–bearing urethral grafts using the neodymium:yag surgical laser," Journal of Urology, vol. 146, pp. 840–842, Sep. 1991.

L. Goldman, Biomedical Aspects of the Laser, Springer–Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S–92–S–93, Jan.–Feb. 1965.

L. Goldman, "Effects of new laser systems on the skin," Arch Dermatol., vol. 108, pp. 385–390, Sep. 1973.

L. Goldman, "Laser surgery for skin cancer," New York State Journal of Medicine, pp. 1897–1900, Oct. 1977.

L. Goldman, "Surgery by laser for malignant melanoma," J. Dermatol. Surg. Oncol., vol. 5, No. 2, pp. 141–144, Feb. 1979.

L. Goldman, "The skin," Arch Environ Health, vol. 18, pp. 434–436, Mar. 1969.

L. Goldman & D.F. Richfield, "The effect of repeated exposures to laser beams," Acta derm.–vernereol., vol. 44, pp. 264–268, 1964.

L. Goldman & R.J. Rockwell, "Laser action at the cellular level," JAMA, vol. 198, No. 6, pp. 641–644, Nov. 1966.

L. Goldman & R.G. Wilson, "Treatment of basal cell epithelioma by laser radiation," JAMA, vol. 189, No. 10, pp. 773–775.

L. Goldman et al., "The biomedical aspects of lasers," JAMA, vol. 188, No. 3, pp. 302–306, Apr. 1964.

L. Goldman et al., "Effect of the laser beam on the skin, Preliminary report" Journal of Investigative Dermatology, vol. 40, pp. 121–122, 1963.

L. Goldman et al., "Effect of the laser beam on the skin, III. Exposure of cytological preparations," Journal of Investigative Dermatology, vol. 42, pp. 247–251, 1964.

L. Goldman et al., "Impact of the laser on nevi and melanomas," Archives of Dermatology, vol. 90, pp. 71–75, Jul. 1964.

L. Goldman et al., "Laser treatment of tattoos, A preliminary survey of three year's clinical experience," JAMA, vol. 201, No. 11, pp. 841–844, Sep. 1967.

L. Goldman et al., "Long–term laser exposure of a senile freckle," ArchEnviron Health, vol. 22, pp. 401–403, Mar. 1971.

L. Goldman et al., "Pathology, Pathology of the effect of the laser beam on the skin," Nature, vol. 197, No. 4870, pp. 912–914, Mar. 1963.

L. Goldman et al., "Preliminary investigation of fat embolization from pulsed ruby laser impacts of bone," Nature, vol. 221, pp. 361–363, Jan. 1969.

L. Goldman et al., "Radiation from a Q–switched ruby laser, Effect of repeated impacts of power output of 10 megawatts on a tattoo of man," Journal of Investigative Dermatology, vol. 44, pp. 69–71, 1965.

L. Goldman et al., "Replica microscopy and scanning electron microscopy of laser impacts on the skin," Journal of Investigative Dermatology, vol. 52, No. 1, pp. 18–24, 1969.

M.C. Grossman et al., "Damage to hair follicles by normal–mode ruby laser pulses," Journal of he American Academy of Dermatology, vol. 35, No. 6, pp. 889–894, Dec. 1996.

E. Klein et al., "Biological effects of laser radiation 1.,"Northeast Electronics Research and Engineering Meeting, NEREM Record, IEEE catalogue No. F–60, pp. 108–109, 1965.

J.G. Kuhns et al., "Laser injury in skin," Laboratory Investigation, vol. 17, No. 1, pp. 1–13, Jul. 1967.

J.G. Kuhns et al., "Biological effects of laser radiation II Effects of laser irradiation on the skin," NEREM Record, pp. 152–153, 1965.

R.J. Margolis et al., "Visible action spectrum for melanin–specific selective photothermolysis," Lasers in Surgery and Medicine, vol. 9, pp. 389–397, 1989.

J.A. Parrish, "Selective thermal effects with pulsed irradiation from lasers: From organ to organelle," Journal of Investigative Dermatology, vol. 80, No. 6 Supplement, pp. 75s–80s, 1983.

L. Polla et al., "Melanosomes are a primary target of Q–switched ruby laser irradiation in guinea pig skin," Journal of Investigative Dermatology, vol. 89, No. 3, pp. 281–286, Sep. 1987.

T. Shimbashi & T. Kojima, "Ruby laser treatment of pigmented skin lesions," Aesth. Plast. Surg., vol. 19, pp. 225–229, 1995.

Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F–60, pp. 150–151, Nov. 1965.

C.R. Taylor et al., "Treatment of tattoos by Q–switched ruby laser," Arch. Dermatol. vol. 126, pp. 893–899, Jul. 1990.

V.V. Tuchin, "Laser light scattering in biomedical diagnostics and therapy," Journal of Laser Applications, vol. 5, No. 2–3, pp. 43–60, 1993.

S. Watanabe et al, "Comparative studies of femtosecond to microsecond laser pulses on selective pigmented cell injury in skin," Photochemistry and Photobiology, vol. 53, No. 6, pp. 757–762, 1991.

A.J. Welch et al., "Evaluation of cooling techniques for the protection of the pidermis during HD–yag laser irradiation of the skin," Neodymium–Yag Laser in Medicine and Surgery, Elsevier Science Publishing Co., publisher, pp. 195–204, 1983.

R.B. Yules et al., "The effect of Q–switched ruby laser radiation on dermal tattoo pigment in man," Arch Surg, vol. 95, pp. 179–180, Aug. 1967.

E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1–18, 1971.

Abstract Nos. 17–19, Lasers in Surgery and Medicine, ASLMS, Supplement 13, 2001.

Abstract Nos. 219–223, ASLMS.

Abstracts, various.

Invention description to certificate of authorship, No. 532304, "The way of investigation of radiation time structure of optical quantum generator".

Invention description to certificate of authorship, No. 719439, "The ring resonator of optical quantum generator".

Invention description to certificate of authorship, No. 741747, "The modulator of optical radiation intensity".

Invention description to certificate of authorship, No. SU 1257475 A1, "Laser interferometric device to determine no–linearity of an index of refraction of optical medium".

Invention description to certificate of authorship, No. SU 1326962 A1, "The way of determination of non–linearity of an index of refraction of optical medium".

IPG Photonics Data Sheet for Thulium Fiber Laser, Jun. 2001, Parameters and Technical Specifications.

* cited by examiner

FIBER LASER DEVICE FOR MEDICAL/COSMETIC PROCEDURES

RELATED APPLICATIONS

This non-provisional application claims the benefit under Title 35, U.S.C. §119(e) of U.S. Provisional Application Ser. No. 60/302,426, filed Jul. 2, 2001, entitled "Optical Radiation Device for Medical/Dermatological Procedures with Frequency Control," by G. Altshuler, incorporated herein by reference.

FIELD OF THE INVENTION

This invention relates to laser devices for medical and cosmetic procedures and more particularly to such devices utilizing a tunable and/or fiber laser as a radiation source.

BACKGROUND OF THE INVENTION

Laser and other optical radiation sources are utilized in devices for performing a variety of dermatology and other medical/cosmetic procedures. Such procedures typically target a chromophore in the tissue of the individual being treated which, depending on the procedure, may be melanin, hemoglobin, lipid, water, pigment of a tattoo etc. Since water is the major constituent of cells in an individual's skin, water is frequently the chromophore of choice in performing such procedures.

Water being highly absorbent at many optical radiation wavelengths, particularly wavelengths over about 1800 nm, can be a very efficient absorber of optical radiation at these and other wavelength bands, therefore permitting a desired procedure, particularly a dermatology procedure, to be performed from a source having relatively low output energy, and thus from a source which is smaller and less expensive than where a chromophore which absorbs less strongly is targeted or where the wavelength utilized is not as strongly absorbed by water. However, the pervasiveness of water in skin means that radiation at wavelengths highly absorbed by water can penetrate at most a few millimeters into a patient's skin. Some dermatology or other procedures performed by targeting water require deeper penetration.

Heretofore, it has not been possible to obtain optimum efficiency for a laser dermatology or other procedure targeting water at a variety of depths from a single laser device, and in particular, it has not been possible to scan the treatment laser beam in the depth direction during a treatment procedure.

Focus is also an issue in targeting a particular depth, the relatively large spot sizes of existing devices making it difficult to focus to a precise 3D spot. In addition, some desirable wavelengths are difficult and/or expensive to achieve with existing lasers.

An improved treatment device with a smaller, more easily focused spot size is therefore desirable, as is such a device permitting a range of wavelengths to be easily and controllably achieved so as to facilitate a desired depth of penetration while achieving optimum radiation absorption, and more efficient treatment at the desired depth. An ability to scan in the depth direction is also desirable.

SUMMARY OF THE INVENTION

In accordance with the above, the invention provides a device and a method for performing radiation treatment on a patient. The device may include at least one fiber laser and a mechanism for delivering radiation from the at least one fiber laser to the patient. Where the fiber laser is tunable, the device may also include controls for tuning the fiber laser to a desired wavelength. The desired wavelength may be selected a desired depth of penetration in the patient and/or a selected laser efficiency. The controls may also scan radiation depth by the controls scanning the laser wavelength. The controls, which may be either manually or computer controlled, may also change absorption, and thus target heating, by changing wavelength.

A plurality of the fiber lasers may be adjacent mounted to provide radiation along a line, and the lasers may be spaced to achieve selected spaced areas of damage in a target region. For selected embodiments, the tunable range is at least 1800 to 1920 nm. For some embodiments, the device includes a box containing part of the at least one fiber laser along with drivers and controls therefore, a handpiece containing an end of the at least one fiber laser and optics which are at least part of the mechanism for delivering radiation from the fiber laser to the patient, and an umbilical through which the at least one fiber laser passes from the box to the handpiece. The box may also include a mechanism for tuning the wavelength of the fiber laser(s). For other embodiments, the device is a substantially self-contained handheld device containing the at least one fiber laser, a driver mechanism and a control mechanism therefore, and optics which form at least part of the mechanism for delivering radiation from the fiber laser to the patient. For these embodiments, the control mechanism preferably includes a mechanism for tuning the wavelength of the fiber laser(s).

The method includes providing at least one fiber laser, and delivering optical radiation from the at least one fiber laser to a portion of a patient's body undergoing treatment. The step of tuning the fiber laser(s) to a desired wavelength, either before or during the delivery step, is also preferably provided. The wavelength may also be scanned during the delivery step, thereby causing depth of penetration to be scanned.

The method and device are preferably used to perform a dermatology procedure, and in particular may be utilized to treat at least one of vascular lesions, non-uniformity of skin pigmentation, unwanted hair, acne, tattoos, nail cosmetics and disorders, skin micro-preparation/micro-perforation, improving skin appearance/texture, vitiligo, psoriasis and tissue welding. The method and device may also be implemented using any suitable tunable laser.

The foregoing and other objects, features and advantages of the invention will be apparent from the following more particular description of preferred embodiments of the invention, as illustrated in the accompanying drawings, the same or similar reference numerals being used for common elements in the various figures.

DETAILED DESCRIPTION OF THE INVENTION

Figure 1A:
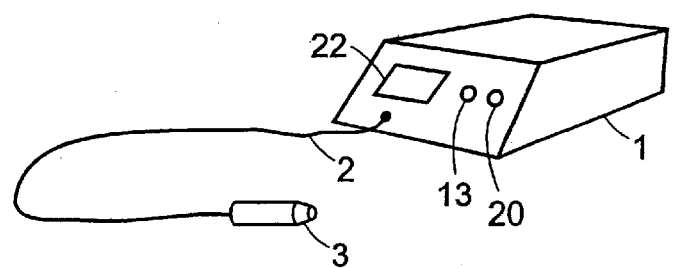
FIG. 1 shows one embodiment of the invention, FIG. 1a being a schematic view of the system of the embodiment, FIG. 1b being a cut-away side view of a handpiece suitable for use in this embodiment, and FIG. 1c being a cut-away side view of a handpiece comprising a plurality of fiber lasers.

The problems indicated above are overcome in accordance with the teachings of preferred embodiments of this invention by utilizing as the radiation source a fiber laser with diode pumping, for example fiber lasers from IPG Photonics Corporation (Oxford, Mass.). Depending on application, a single fiber laser having an output power of up to 2000 W may be utilized, or two or more such lasers may be utilized. Such high power can be achieved with a Ytterbium (Yb) fiber laser. The wavelength of this laser is about 1070 nm. Other fiber lasers available include ones doped with different ions such as Thulium (Tm), Erbium (Er), Praseodymium (Pr), Nedimium (Nd) and Holmium(Ho). In Table 1, parameters of various ones of these fiber lasers are show. The main advantages of fiber lasers are high efficiency (up 30%), high beam quality and brightness (diffraction limited), compactness, high reliability, tunability and potential low cost.

applied to head handpiece 3 through umbilical 2 from box 1. All of handpiece 3, except for tip 8, is shown enclosed in a housing 7, which housing may be grasped by a system operator. Handpiece 3 is shown positioned against the skin 9 of a patient. Electronics in box 1 can provide optical radiation in CW or pulsing mode, including Q-switch mode.

Figure 1B:
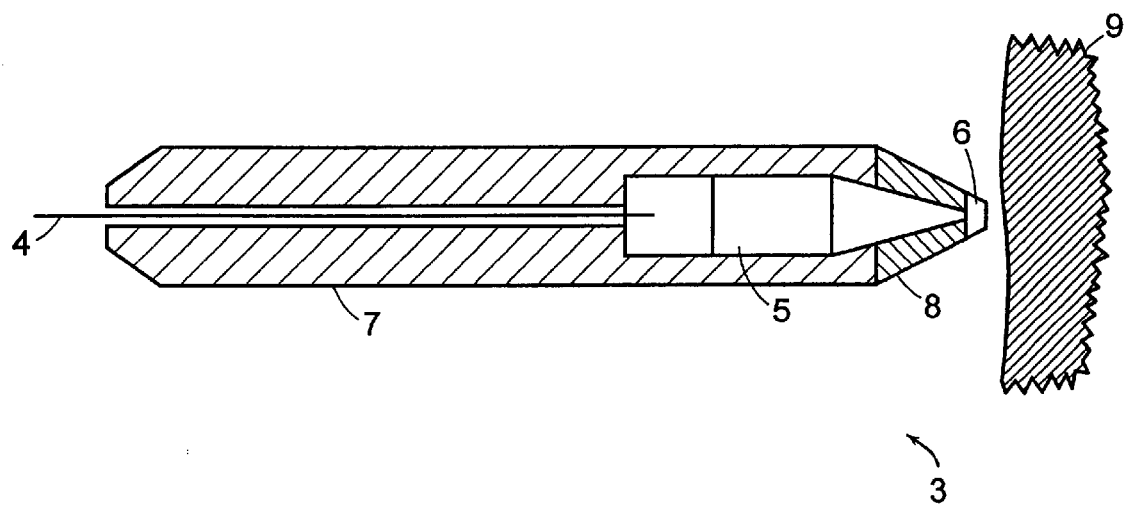
Figure 1C:
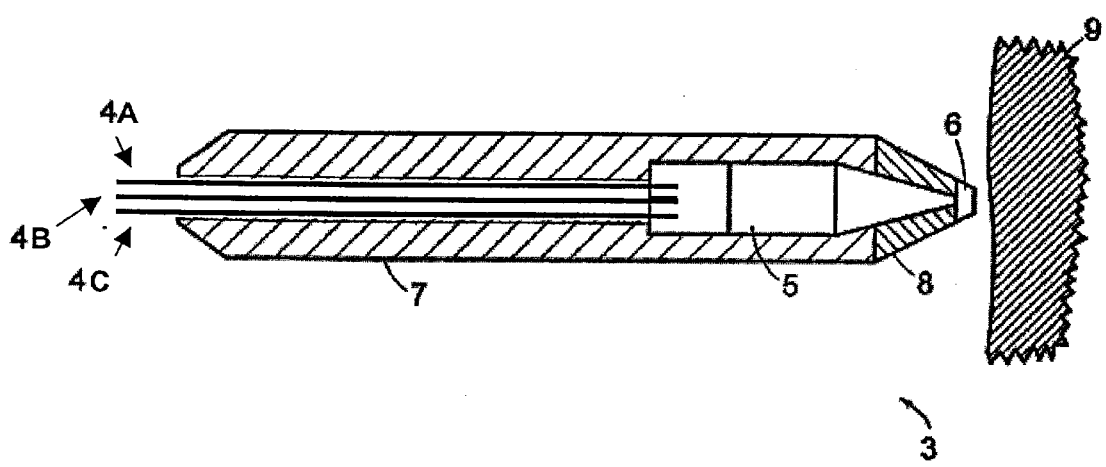
Figure 2:
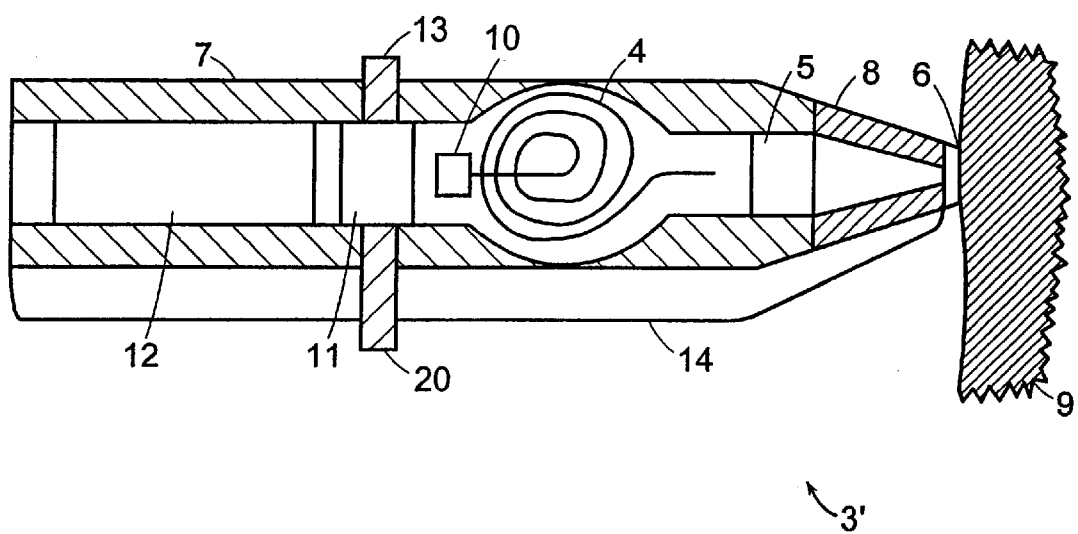
FIG. 2 is a cut-away side view of a self-contained handpiece for a second embodiment of the invention.

FIG. 2 shows a self contained or handpiece version 3' of a fiber laser based system, which system would normally be used for cosmetic treatments. Handpiece 3' includes a diode laser 10 driving a fiber laser 4 under control of control electronics 11. A battery 12 provides power for all of these components. Electronics 11 has an on/off switch 13 and a tuning control 20 for the illustrative embodiment; however, either or both of these controls may be missing for some embodiments, particularly where tuning of fiber laser 4 is not required. An on/off switch is also shown for the embodiment of FIG. 1. A cooling element 14 is shown, which may be used to cool the laser(s), other electronic components and/or tip 6. Cooling element 14 can be a phase transfer material as described in copending application entitled "Cooling System for a Photocosmetic Device," by J. Caruso, G. Altshuler, H. Zenzie, J. Burke, A. Erofeev, filed May, 23, 2002, which is incorporated herein in its entirety by reference, or a liquid gas. Power for diode 10 can be 1W for an illustrative embodiment. The fiber laser output for such illustrative embodiment can have an 0.2 W power density,

TABLE 1

| Parameters | Yb laser | Tm laser | Pr laser | Er laser | Ho laser |
|---|---|---|---|---|---|
| Power, W | Up to 2000 | Up to 15 | Up to 10 | Up to 5 | Up to 1 |
| Wavelength, nm | 1050–1120 | 1450–1610 1750–2000 | 1290–1315 | 1520–1610 | 2.85–2.95 3.2 |
| Wavelength with Raman converter, nm | 1200–1600 | | | | |
| Wavelength with second harmonic generator, nm | 525–555 | 725–805 875–1000 | 645–657 | 760–805 | 1.42–1.47 1.6 |
| Energy in Q-switch mode, J | 0.005 | | | | |
| Beam quality, $M^2$ | <1.05 | | | | |
| Minimum spot size on the target, microns | 1–30 | | | | |

The wavelength of a fiber laser can be easily converted to another wavelength by using non-linear optics, for example a non-linear crystal or fiber for second harmonic generation (SHG) or an optical parametric oscillator (OPO). With this option, the operating wavelength of a fiber laser may cover the hemoglobin absorption band (Yb laser with SHG 525–555 nm).

A desktop version of a medical or cosmetic system based a fiber laser is shown in FIG. 1a. This system includes a box 1 which contains control and other electronics, a cooling mechanism, a diode laser, part of a fiber laser, suitable optics and an acoustic module for tuning the wavelength of the fiber laser if it is necessary. The system also includes a handpiece 3 connected to box 1 by an umbilical 2 having fiber laser 4 passing therethrough. Referring to FIG. 1b, which is a cross section of handpiece 3, it is seen that the end of fiber laser 4 extends inside the handpiece, terminating at optical system 5, which may include lenses, and, if necessary, non-linear optics and/or a 1D, 2D or 3D beam scanner. The handpiece also includes an optical tip 6 which can include a sapphire plate or lens, mounted within a mechanical support 8. A cooling function may be provided to tip 6, generally through support 8, in various ways known in the art, for example electronically or by flowing cooling liquid or gas over the tip, the cooling fluid normally being have a 5 micron spot size and deliver 1 MW/cm$^2$ or 10000 J/cm$^2$ for a 10 ms pulsewidth.

The embodiment of either FIG. 1 or FIG. 2, may contain a single fiber laser 4 mounted to generate a spot output, or may contain two or more of the fiber lasers 4 mounted adjacent each other to generate an output along a line. Such a configuration of plurality of fiber lasers is shown in FIG. 1C, where lasers 4A, 4B and 4C are mounted adjacent to each other. If a battery 12 is not utilized, electrical energy may be applied to the handpiece of FIG.2 through an umbilical to drive the various components thereof. Optoacoustic or other suitable elements known in the art may be utilized to tune the wavelength of the fiber laser. A suitable manual control 20 may be provided, for example as shown in each figure, to permit the operator to control the output frequency from the fiber laser. Suitable cooling may also be provided for the handpiece either through umbilical 2 or by a thermoelectric or other component mounted in the handpiece. Box 1 or electronics 11 may include a microprocessor or other suitable control for automatically, for example by a suitable program, controlling fiber laser output. A display, for example display 22 in FIG. 1a, may be provided for either embodiment to show the operator the frequency to which the fiber laser is tuned and/or other relevant information.

Figure 3:
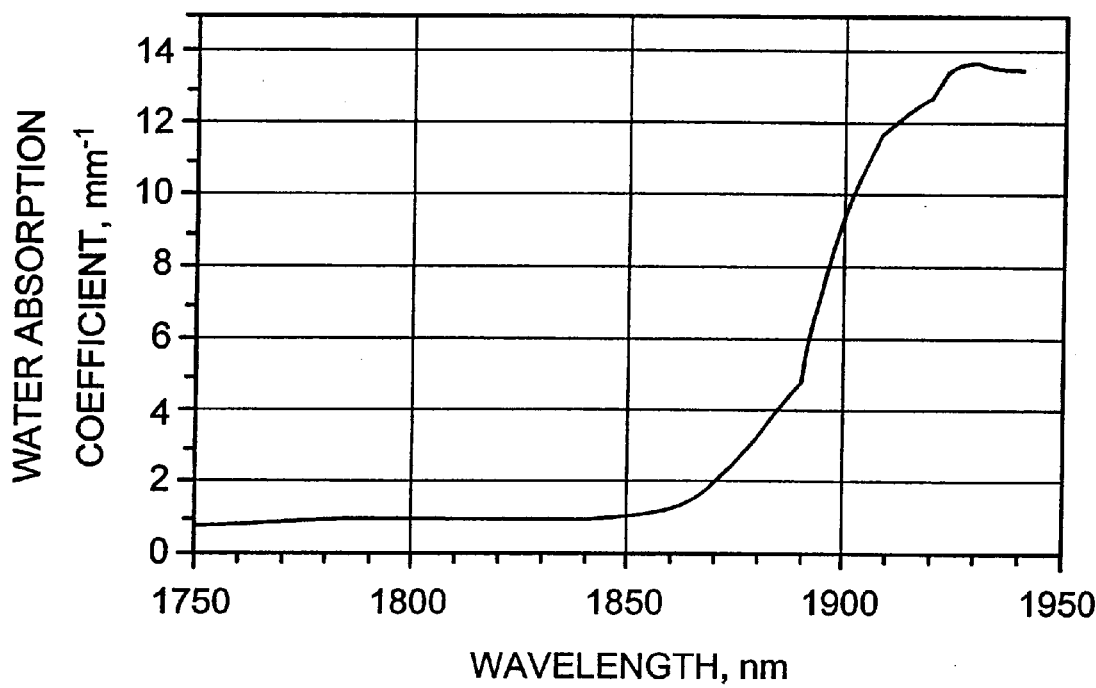
FIG. 3 is a diagram showing the relationship between water absorption coefficient and wavelength over a relevant wavelength band.

FIG. 3 is a diagram illustrating the absorption characteristics of water, particularly water in tissue, from 1750 to 1950 nm. Available fiber lasers currently provide an output tunable over a range of approximately 1750 to 2000 nm. From FIG. 3, it can be seen that absorption by water is roughly 1 mm$^{-1}$ from about 1750 to 1860 nm, and then increases significantly to nearly 14 mm$^{-1}$ as a function of wavelength from 1860 to approximately 1920 nm. Laser efficiency in heating water at 1860 nm, while adequate for most applications, is substantially lower than for a wavelength of approximately 1920 nm. However, depth of penetration is less at this more highly absorbed wavelength. By adjusting control 20, the user can therefore tune fiber laser 4 to obtain optimum laser efficiency for a desired depth of penetration and can control the depth of penetration which is achieved. The radiation can also be scanned in the depth direction either by manually adjusting control 20, or automatically where a processor is provided and is utilized to control the output wavelength of the fiber laser. The processor may be programmed for a desired scan pattern or may control the scan in response to suitable inputs from a user, for example operation of control 20.

Another advantage of fiber laser 4 is that it produces a small spot size, for example five mm, which may be more easily focused to a precise point at a precise depth. Particularly where two or more of these fibers are positioned in handpiece 3, adjacent to but spaced from each other, the invention may be used to achieve precise areas of damage/sparing as taught in co-pending application Ser. No. 10/033302, filed Dec. 27, 2001, which is incorporated herein in its entirety by reference.

Still another advantage of using a tunable fiber laser 4 for optical dermatology is that it can be tuned to wavelengths which are desirable but otherwise difficult and/or expensive to achieve. For example, the 1920 nm wavelength achievable with this device has previously been achieved only with an expensive and low efficiency Holmium laser.

Further, when it is desired to change target temperature, it has been necessary to alter laser power, something which is not always easy, and generally involves an appreciable time delay before the desired target temperature change is achieved; however, changing wavelength in accordance with the teachings of this invention can cause a rapid and significant change in target absorption, and thus in target temperature. Such a mechanism for controlling target temperature has not heretofore been available.

While the devices of this invention have many potential therapeutic and cosmetic applications, they are particularly adapted for various dermatological treatments including:

(a) Skin treatments/rejuvenation including: treating vascular lesions, such as spider veins, the precise spot size being particularly adapted for the selective coagulation of vessels, treating non uniformity of skin pigmentation, treating skin collagen to for example improve skin appearance and/or feel/texture, skin micro-preparation/poration, etc.

(b) hair removal.

(c) treating acne, particularly by the destruction of the sebaceous gland.

(d) treating of nails (e) tattoo removal.

(f) tissue welding.

Figure 4:
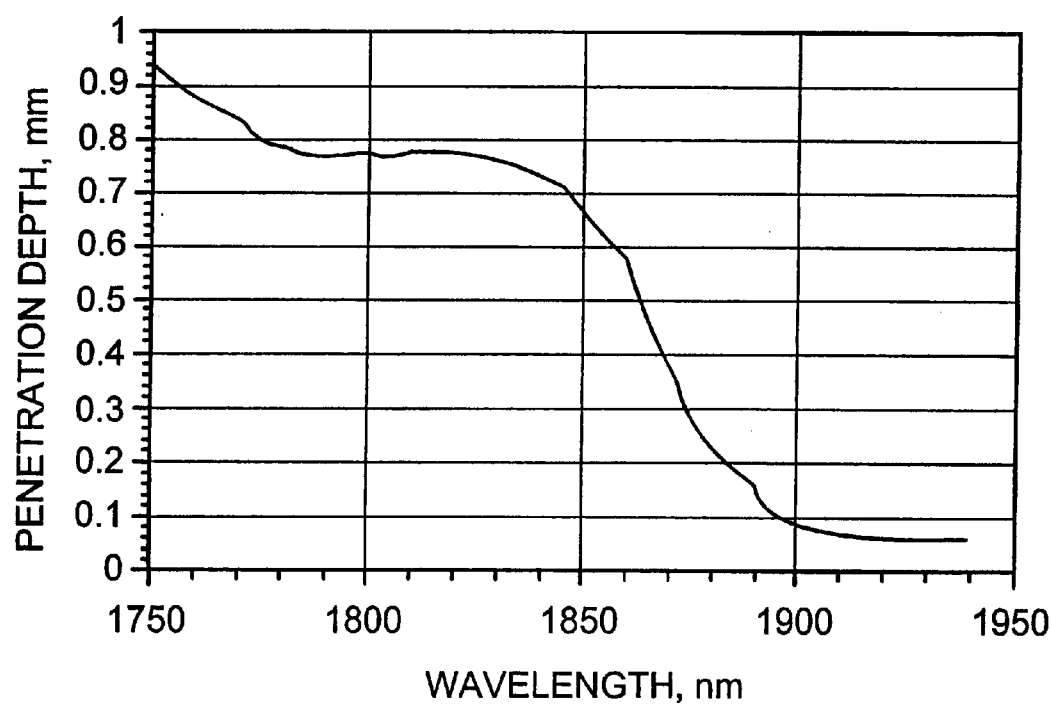
FIG. 4 is a diagram showing the relationship between penetration depth of light into the human dermis and wavelength.
Figure 5:
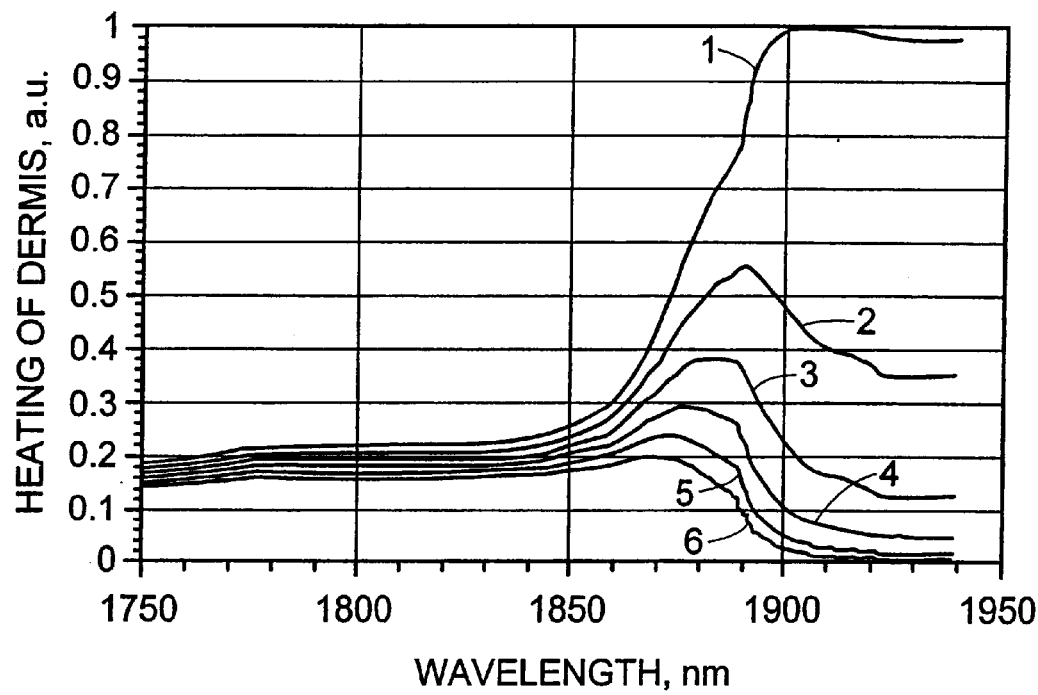
FIG. 5 is a diagram showing the relationship between adiabatic heating of the dermis at various depths and wavelength.
Figure 6:
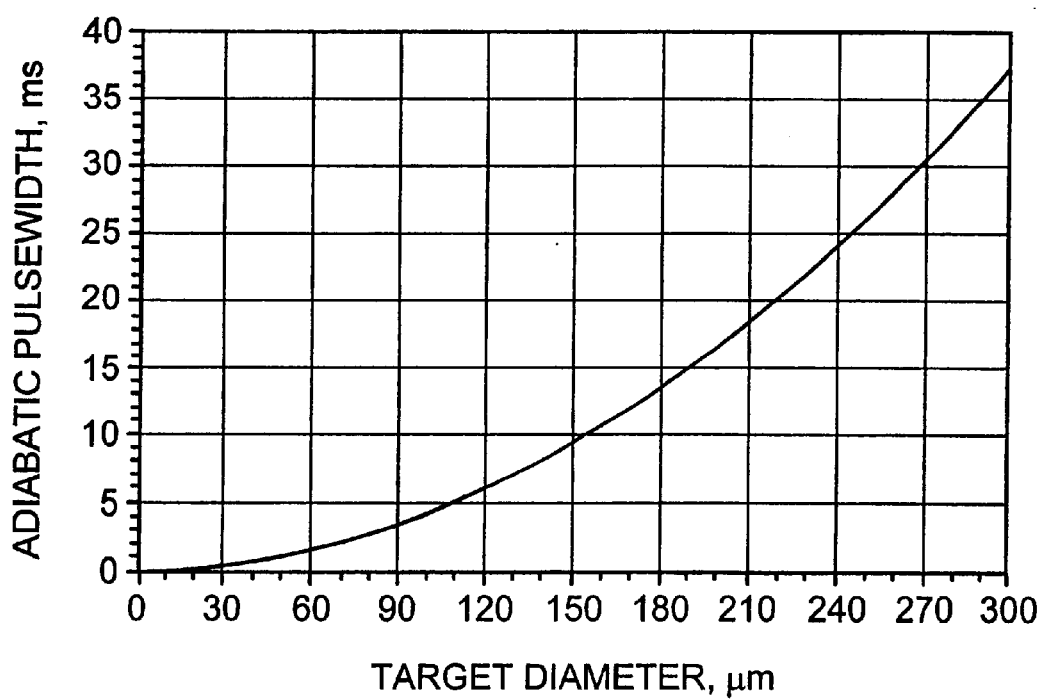
FIG. 6 is a diagram showing the relationship of adiabatic pulse width and target diameter under certain assumptions.

Considering some of these treatments in greater detail:

Skin rejuvenation:

The system of for example an IR tunable fiber laser, focusing optics, and (in some embodiments) scanner (or other embodiments) can be used for treatment of various skin conditions, including (but not limited to) vascular lesions, pigmented lesions, vitiligo, psoriasis, and for improving skin texture. Targeting the laser beam at a specific depth is achieved by changing the focal length of the focusing optics and tuning the laser to a specific wavelength. Since scattering in the tunable wavelength range is drastically reduced in comparison to the visible wavelength range, beam shaping is possible at much greater depths, with a soft focus being possible to even greater depths. As a result, a focal spot can be created at a desired depth down to at least about 1 mm below the surface. Since water is the primary chromophore in the tunable wavelength range, practically any structure within the specified depth range can be targeted. When treating pigmented lesions, the laser is operated in such a way as to cause either ablation or coagulation of tissue in the selected area in the pigmented lesion. When treating vascular lesions, blood is coagulated as a result of heating water in the blood vessels, and closure of the vessel is achieved. When improving skin texture, the laser is operated at sub-coagulation fluence levels and focused in the upper dermis in order to induce a micro-inflammatory reaction and increase collagen production in the targeted area. When treating vitiligo, the laser is focused in the basal membrane and operated at sub-coagulation levels in order to induce an increase in melanin production. When treating psoriasis, the laser is also focused in the basal membrane and operated at a fluence level sufficient to suppress hyper-proliferation activity of the basal cells. Within the scope of this invention, other treatment regimens can be devised by those skilled in the art for treatment of these and other skin conditions. FIGS. 4 and 5 illustrate how it is possible, by changing the wavelength of the fiber laser, to concentrate light, and thus heat, at different depths in the skin. FIG. 6 illustrates the relationship between adiabatic pulse-width and target diameter, where the target is assumed to be spherical, and the adiabatic pulse-width is assumed to coincide with the thermal relaxation time, yielding:

$$\text{pulsewidth} = \frac{D^2}{24 \cdot \alpha}$$

with $\alpha = 10^{-3}$ cm$^2 \cdot$s$^{-1}$.

Skin Micropreparation/microperforation

The purpose of this aspect of the invention is to provide a minimally invasive technique for creating a highly reproducible and controlled micro-perforation pattern in tissue (typically, in skin). This goal can be achieved by using an IR tunable fiber laser with focusing optics yielding a spot size of about 5 $\mu$m at the skin surface. The laser can be tuned within a wavelength range between 1.75 $\mu$m and 1.94 $\mu$m. When operated at a sub-millisecond pulse-width range, the skin ablation threshold is about 1.5 kJ/cm$^2$. That requires the output energy of about 0.4 $\mu$J. Unlike previously disclosed laser systems for fluid sampling, the small channel diameter delivered by the proposed technique precludes any blood loss and greatly diminishes the danger of the channel contamination by exogenous microorganisms. The small channels also facilitate fast healing. At the same time, the channel is sufficient to facilitate penetration of pharmaceutical or cosmetic compositions through the stratum corneum.

In some embodiments of the invention, the laser is combined with a scanning system, providing a capability of creating highly controlled micro-perforation patterns.

Acne

In yet another aspect of the invention, the system of an IR tunable fiber laser, focusing optics, and (in some embodiments) scanner can be used for the treatment of acne. When treating acne, the system is focused either in the sebaceous gland itself to suppress sebum production or in the infundibulum to reduce clogging of the sebaceous duct. In this application, additional selectivity can be achieved by tuning the fiber laser to a wavelength close to the absorption maximum of lipids (around 1.75 $\mu$m).

Nail Cosmetic/disorders

In yet another aspect of the invention, the system of an IR tunable fiber laser, focusing optics, and (in some embodiments) scanner can be used for treatment of nail disorders (including, as examples, fungal infection and paronychia) and for cosmetic/hygienic reshaping of nail plates. When treating nail disorders, the system is focused in the pockets of infection, and the causative agents (fungi or bacteria) are killed through photothermal action. When using the system to improve cosmetic appearance of the nails and/or hygienic conditions of the nails, light is focused within the nail plate, and either the microstructure of the plate is modified to alter its visual appearance, or multiple pulses are used to cause separation of unwanted parts of the plate.

Tattoo Removal

A fiber laser in Q-switch mode and tuned to an optimum wavelength to match the spectra of absorption of a tattoo can be used for tattoo removal. The wavelength of the fiber laser can be selectively changed to match variations in coloring of the portion of the tattoo being treated.

While the invention has been described above with respect to illustrative embodiments and variations thereon, the particular fiber lasers described, as well as the handpiece 3 and the overall system, are provided for purposes of illustration only and can vary significantly with application. In particular, while diode pumping of the fiber laser and acoustic tuning are specified for preferred embodiments, these are not limitations on the invention, and, where appropriate, other suitable pumping and tuning mechanisms may be utilized. Optics, cooling and other components can also vary with application. Further, while fiber lasers are required for most embodiments, there are embodiments where such lasers may not be required. Finally, while the invention is particularly adapted for dermatology applications, it may also be utilized to perform other medical/therapeutic and/or cosmetic procedures. Thus, the foregoing and other changes may be made in the invention by those skill in the at while still remaining within the spirit and scope of the invention which is intended to be limited only by the following claims.

What is claimed is:

1. A device for performing a radiation treatment on a patient comprising:
   at least one fiber laser;
   a mechanism for delivering radiation from the at least one fiber laser to the patient at a desired wavelength; and
   controls for tuning the at least one fiber laser to the desired wavelength and for changing the desired wavelength during treatment, said controls including a processor programmable to scan the wavelength to vary the depth of penetration.

2. A device as claimed in claim 1, wherein said desired wavelength is selected to achieve at least one of a desired depth of penetration in patient and a selected laser efficiency.

3. A device as claimed in claim 1, wherein said controls change the desired wavelength of the at least one fiber laser, and thus scan radiation depth.

4. A device as claimed in claim 1, wherein said controls are at least one of manual and computer controlled.

5. A device as claimed in claim 1, wherein said controls, by changing the desired wavelength, change absorption, and thus target heating.

6. A device as claimed in claim 1, wherein said at least one fiber laser is tunable over a range of at least 1800 to 1920 nm.

7. A device as claimed in claim 1 wherein said device includes a box containing part of said at least one fiber laser along with drivers and controls therefore, a head containing an end of said at least one fiber laser and optics which are at least part of said mechanism for delivering radiation from the fiber laser to the patient, and an umbilical through which the at least one fiber laser passes from the box to the head.

8. A device as claimed in claim 7 wherein said box includes a mechanism for tuning the desired wavelength of the at least one fiber laser.

9. A device as claimed in claim 1 wherein said device is utilized to treat at least one of vascular lesions, non-uniformity of skin pigmentation, unwanted hair, acne, tattoos, nail cosmetics and disorders, skin micro-preparation/micro-perforation, improving skin appearance/texture, vitiligo, psoriasis and tissue welding.

10. A device for performing a radiation treatment on a patient comprising:
    a plurality of fiber lasers mounted adjacent to each other to provide radiation along a line; and
    a mechanism for delivering radiation from said plurality of fiber lasers to said patient.

11. A device as claimed in claim 10, wherein said plurality of fiber lasers are spaced to achieved selected spaced areas of damage in a target region.

12. A device for performing a radiation treatment on a patient comprising:
    at least one fiber laser; and
    a mechanism for delivering radiation from said at least one fiber laser to said patient, wherein said device is a substantially self-contained handheld device containing said at least one fiber laser, a driver mechanism and a control mechanism therefore, and optics which form at least part of said mechanism for delivering radiation from the fiber laser to the patient.

13. A device as claimed in claim 12 wherein said control mechanism includes a mechanism for tuning the wavelength of the at least one fiber laser.

14. A method for performing a laser treatment including:
    providing at least one tunable fiber laser;
    delivering optical radiation from the at least one tunable fiber laser to a portion of a patient's body undergoing the treatment; and
    tuning the at least one tunable fiber laser to change wavelength of optical radiation during said delivering step to scan the depth of penetration.

15. A method as claimed in claim 14 wherein said treatment is a dermatology procedure.

16. A method as claimed in claim 14 wherein said desired wavelength is selected to achieve at least one of a desired depth of penetration in patient and a selected laser efficiency.

17. A method as claimed in claim 14 wherein, by changing the wavelength, target absorption, and thus target heating, are also changed.

18. A method as claimed in claim 14 wherein said method is utilized to treat at least one of vascular lesions, non-uniformity of skin pigmentation, unwanted hair, acne, tattoos, nail cosmetics and disorders, skin micro-preparation/micro-perforation, improving skin appearance/texture, vitiligo, psoriasis and tissue welding.

19. A method for performing a laser treatment including:

providing a plurality of fiber lasers which are positioned to deliver radiation along a line; and delivering optical radiation from the plurality of fiber lasers to a portion of a patient's body undergoing the treatment.

20. A method as claimed in claim 19 wherein the fiber lasers are spaced and radiation therefrom is delivered such that the radiation is delivered to a plurality of spaced spots on the patient's body.

21. A method for performing a laser treatment including:

providing at least one tunable fiber laser;

delivering optical radiation from the at least one fiber laser to a portion of a patient's body undergoing the treatment; and tuning the at least one fiber laser to a desired wavelength suitable for treatment of an identified patient condition either before or during said delivering step.

22. A method for performing a laser treatment including:

providing at least one tunable fiber laser;

delivering optical radiation from the at least one fiber laser to a portion of a patient's body undergoing the treatment; and tuning the at least one fiber laser to a desired wavelength suitable for treatment of an identified dermatological condition either before or during said delivering step, wherein said treatment is a dermatology procedure.

23. A method for performing a laser treatment including:

providing at least one tunable fiber laser;

delivering optical radiation from the at least one fiber laser to a portion of a patient's body undergoing the treatment, wherein a desired wavelength is scanned during said delivering step, thereby causing depth of penetration to be scanned; and tuning the at least one fiber laser to the desired wavelength either before or during said delivering step.

24. A method for performing a laser treatment including:

providing at least one tunable fiber laser;

delivering optical radiation from the at least one fiber laser to a portion of a patient's body undergoing the treatment; and scanning said wavelength during said delivering step, thereby causing depth of penetration to be scanned.

25. A method for performing a laser treatment on a patient including:

tuning at least one laser to a desired wavelength for treatment of an identified dermatological condition;

delivering optical radiation of the desired wavelength from the at least one laser to a portion of a patient's to perform the treatment; and tuning the laser to change the desired wavelength during said delivering step, thereby causing depth of penetration to be scanned.

26. A device for performing a radiation treatment on a patient comprising:

at least one tunable laser;

controls for tuning the laser said controls including a processor programmable to scan the wavelength to vary the depth of penetration; and a mechanism for delivering radiation at the desired wavelength from said at least one laser to said patient.

* * * * *